United States Patent [19]

Schweden et al.

[11] Patent Number: 5,919,762
[45] Date of Patent: Jul. 6, 1999

[54] CONJUGATES OF HIRUDIN AND LIPOPHILIC COMPOUNDS

[75] Inventors: Jürgen Schweden, Neustadt; Peter Eckes, Otterstadt; Wilfried Hornberger, Neustadt; Thomas Subkowski, Mutterstadt, all of Germany

[73] Assignee: BASF Aktiengesellschaft, Ludwigshafen, Germany

[21] Appl. No.: 08/652,511

[22] PCT Filed: Nov. 25, 1994

[86] PCT No.: PCT/EP94/03901

§ 371 Date: May 31, 1996

§ 102(e) Date: May 31, 1996

[87] PCT Pub. No.: WO95/15183

PCT Pub. Date: Jun. 8, 1995

[30] Foreign Application Priority Data

Dec. 2, 1993 [DE] Germany .................. 43 41 115

[51] Int. Cl.⁶ .................. A61K 38/58; C07K 14/815
[52] U.S. Cl. .................. 514/12; 514/557; 514/558; 530/324; 530/333; 530/345
[58] Field of Search .................. 514/12, 557, 558; 530/324, 333, 345

[56] References Cited

U.S. PATENT DOCUMENTS

| | | | |
|---|---|---|---|
| 4,767,742 | 8/1988 | Dodt et al. | 514/12 |
| 4,810,697 | 3/1989 | Speiser et al. | 514/77 |
| 5,359,030 | 10/1994 | Ekwuribe | 530/303 |

FOREIGN PATENT DOCUMENTS

| | | |
|---|---|---|
| 2067224 | 6/1991 | Canada . |
| 77 529 | 4/1983 | European Pat. Off. . |
| 345 616 | 12/1989 | European Pat. Off. . |
| 40 14 260 | 6/1991 | Germany . |
| WO 91/09837 | 7/1991 | WIPO . |
| 91 14696 | 10/1991 | WIPO . |
| 92 19233 | 11/1992 | WIPO . |

*Primary Examiner*—Douglas W. Robinson
*Assistant Examiner*—Anish Gupta
*Attorney, Agent, or Firm*—Keil & Weinkauf

[57] ABSTRACT

The invention relates to novel hirudin conjugates formed from a hirudin and one or more lipophilic compounds, where the lipophilic compound has an octanol/water partition coefficient of more than 1.8 and is chemically linked to the hirudin, to the preparation thereof and to the use thereof.

7 Claims, 4 Drawing Sheets

CONJUGATES OF HIRUDIN AND LIPOPHILIC COMPOUNDS

The present invention relates to novel hirudin conjugates formed from a hirudin and lipophilic compounds, to the preparation thereof and to the use thereof as drugs.

Hirudin is a naturally occurring protein which has been known for a long time and has anticoagulant properties. It is the strongest and most selective thrombin inhibitor known to date (Naturwissenschaften, 42, (1955), 537; Hoppe-Seylers Z. für Biol. Chemie 366, (1985), 379). Natural hirudin is a mixture of chemically related peptides with a molecular weight of 6,900–7,000 daltons and 64–66 amino acids. To date about 20 naturally occurring hirudin variants have been described (Scharf et al., FEBS-Letters 255, (1989), 105–110).

EP 345616 describes products composed of hirudin coupled to polymeric carriers. Carriers which are mentioned are soluble and insoluble polymers such as dextran, Sepharose, heparin, levan and gelatin partial hydrolysate. The carrier-modified hirudins are said to have improved pharmacological properties such as a longer half-life.

DE 40 14 260 describes hirudin/polyalkylene glycol conjugates which, compared with natural hirudin, have a more favorable pharmacological profile of action, for example a prolonged biological activity and a better bioavailability.

Both the abovementioned patent applications describe hirudin derivatives with prolonged activity achieved by modifying the hirudin with a high molecular weight polymer. The molecular weight of the polymer in these cases amounts to several kilodaltons so that there is a considerable increase in the molecular weight of the polypeptide hirudin. However, high molecular weight polymers of these types are not exactly defined chemically; on the contrary they comprise a population of various molecules distributed over a molecular weight range. Accordingly, the hirudin coupling products prepared therewith are not composed of a single chemical compound either, on the contrary they are composed of populations of molecules which differ from one another in their molecular weight.

However, it is desirable that active substances which are used as drugs be chemically defined as exactly as possible in order to allow their behavior in the body to be controlled better.

Figure 1:
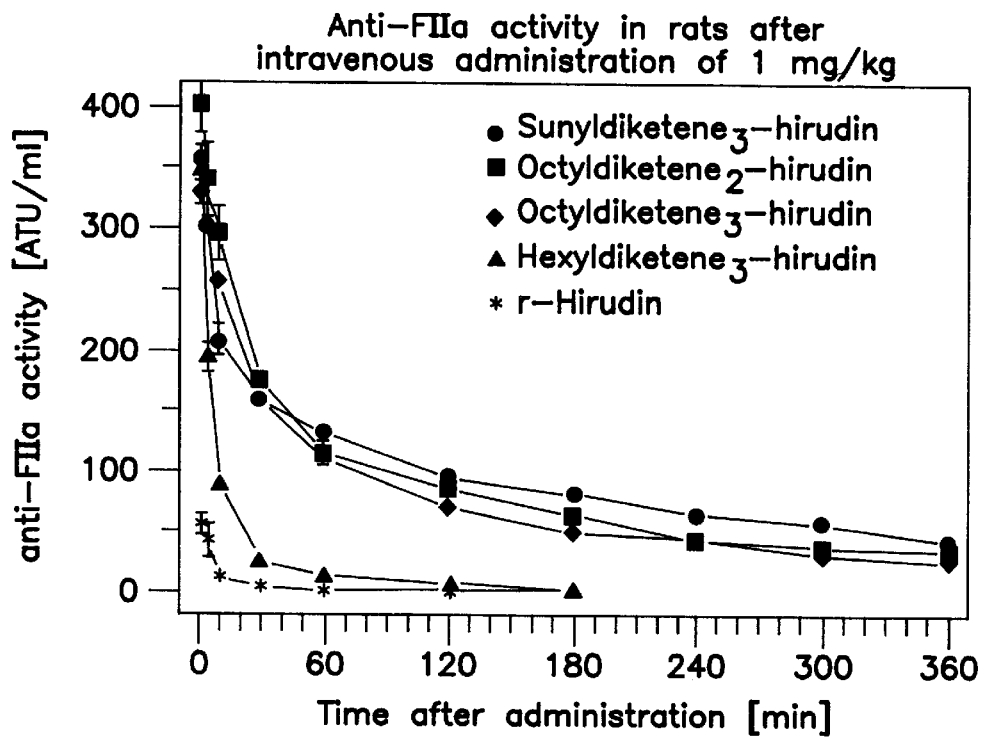
FIG. 1: Anti-FIIa activity in rats after intravenous administration of 1 mg/kg of Sunyldiketene$_3$-hirudin, Octyldiketene$_2$hirudin, Octyldiketene$_3$-hirudin, Hexyldiketene$_3$-hirudin, and r-Hirudin.

It is an object of the present invention to provide hirudin derivatives which have pharmacological properties which are better than those of normal hirudin and which do not have the abovementioned disadvantages of the hirudins modified with high molecular weight polymers.

We have found that this object is achieved by hirudin conjugates formed from a hirudin and one or more lipophilic compounds, where the lipophilic compound has an octanol/water partition coefficient of more than 1.8 and is covalently linked to the hirudin.

Suitable for the hirudin conjugates according to the invention are all naturally occurring hirudins as well as variants derived from them, called hirudin muteins, and fragments with a thrombin-inhibiting effect.

Hirudins of these types and their preparation are disclosed, for example, in EP 171 024, EP 158 986, DE 38 055 406, WO 92/1712, GB 2 247 239, EP 557 199, WO 92/5748, DE 40 14 260.

Also very suitable for preparing the hirudin conjugates according to the invention are peptides or peptide derivatives which have structures derived from that of hirudin and have hirudin activity, as described, for example, in EP 333 356.

Hirudins which are preferably used are those in which the linkage of the lipophilic compound leads to no loss of activity. This is the case, for example, in hirudins where the linkage takes place via side chains of amino acids 27 to 37. Particularly advantageous for the linkage are amino acid positions 27 and 33 (based on natural hirudin HVI) because these compounds lie at the tip of a finger-like region and do not interfere with the hirudin/thrombin interaction.

The linkage of the lipophilic compounds, where appropriate of the spacer with the lipophilic compounds, can take place on amino groups of hirudin, for example the free N-terminal amino group, amino groups of the lysine side chains, amino groups of the histidines, amidine groups of the arginines, or on hydroxyl groups of hirudin, for example of tyrosine, serine or threonine side chains.

The amino groups of the lysine side chains are particularly suitable for the linkage of the lipophilic compounds.

It is likewise possible to link the lipophilic compound to a modified tyrosine of hirudin which can be obtained by nitration and reduction (Meth. Enzymol. 25, (1972), 515–521). It is then possible to link the lipophilic compound by known coupling methods to the arylaminotyrosine formed.

Suitable lipophilic compounds are those which have one or more functional groups such as amino, hydroxyl, carboxyl or sulfo groups and which have an octanol/water partition coefficient greater than 1.8.

The lipophilic compounds can be natural substances, e.g. saturated or unsaturated fatty acids, terpenes, prostaglandins, fat-soluble vitamins, carotenoids or steroids, but also synthetic carboxylic acids, alcohols, amines and sulfonic acids with one or more alkyl-, aryl-, alkenyl or else polyunsaturated compounds which can be either linear or branched and may be substituted by halogen, nitro, cyano, alkoxy, alkylthio or haloalkyl groups.

Examples of lipophilic compounds are the saturated fatty acids caproic acid, caprylic acid, capric acid, lauric acid, myristic acid, palmitic acid, stearic acid, arachidic acid and behenic acid and the unsaturated fatty acids palmitoleic acid, oleic acid, linoleic acid, linolenic acid, ricinoleic acid, octadecate-traenoic acid, eicosaenoic acid, eicosadienoic acid, arachidonic acid, eicosapentaenoic acid or erucic acid as well as the fatty alcohols and fatty amines obtainable therefrom.

Also suitable are mixtures of fatty acids as obtained on saponification of natural fats such as coconut fat, palmnut oil, rape oil, olive oil, sunflower oil, high oleic sunflower oil, castor oil or beef tallow.

Other examples of lipophilic compounds are the carotenoids zeaxanthin, rhodovibrin or astaxanthin, the steroids cholesterol, desmosterol, coprosterol, cerebrosterol, lathosterol, ergesterol, sitosterol, stigmasterol, cholanic acid, cholic acid, dehydrocorticosterol, aldosterone, androsterone, testosterone, tachysterol, lanosterol or lumisterol, the terpenes geraniol, nerol, linalool, menthol, carveol, borneol, farnesol, nerolidol or sclareol, the prostaglandins brefeldin, $PGE_2$ or $PGF_2$, vitamins $A_1$ or D as well as synthetic compounds such as oxo alcohols, hexylamine, ethylhexanoic acid, ethylhexanol, ethylhexylamine or alkylbenzenesulfonic acids.

Particularly suitable lipophilic compounds for the invention are those of the general formula I

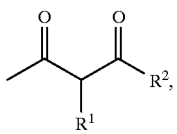

I where $R^1$ and $R^2$ are each, independently of one another, $(CH_2)_m$—$C(R^3)(R^4)$—$(CH_2)_n$—$(CH=CH-CH_2)_o$—$CH_3$, m is 0–28, n is 3–6, o is 0–6, $R^3$ and $R^4$ are each, independently of one another, H, $C_{1-6}$-alkyl, $C_{3-6}$-cycloalkyl, aryl or benzyl, and unsubstituted or substituted by halogen, nitro, cyano, alkyl, alkoxy, alkylthio or haloalkyl groups.

Particularly preferred compounds of the formula I are those in which $R^1$ and $R^2$ comprise 4–16 carbon atoms and are saturated or mono-, di- or triunsaturated.

Further suitable lipophilic compounds are those of the general formula II

H—Y—$R^1$          II where $R^1$ is $(CH_2)_m$—$C(R^3)(R^4)$—$(CH_2)_n$—$(CH=CH-CH_2)_o$—$CH_3$ and Y is —C(O)—, —N($R^5$)—, —O— with $R^5$ being H, $C_{1-18}$-alkyl, $C_{3-18}$-alkenyl, $C_{3-6}$-aryl or benzyl, unsubstituted or substituted by halogen, nitro, cyano, alkyl, alkoxy, alkylthio or haloalkyl groups.

The hirudin conjugates according to the invention are prepared by linking a hirudin either directly or via a spacer to one or more lipophilic compounds.

Suitable spacers are all bi- or multifunctional molecules which, by reason of their multifunctional groups, permit linkage, with or without previous activation, of hirudin and the lipophilic compound.

Particularly suitable spacers are amino acids, oligopeptides, mono-, di- or oligosaccharides, amino or hydroxy carboxylic acids, in particular those with a chain length of 2–10 carbon atoms, which may have further substituents to increase the hydrophilicity, for example $C_1$–$C_4$-oligoalkylene glycols.

Examples of spacers which can be used for linking lipophilic compounds to hirudin are:

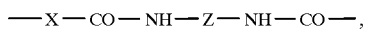

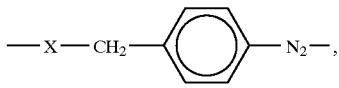

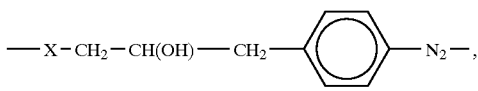

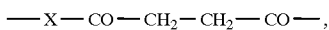

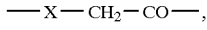

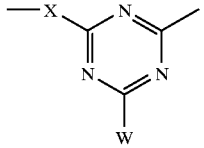

where

X is S, O, NH, $N(CH_3)$ or $N(C_2H_5)$

W is H, OH or Cl

Z is a $C_2$–$C_6$-alkylene group or a p-phenylene group.

It may be necessary to use a spacer in order to retain the biological activity of the hirudin conjugates after binding to surfaces such as cell membranes or synthetic surfaces.

Lipophilic compounds suitable for the hirudin conjugates according to the invention are all those which have one or more functional groups, such as amino, hydroxyl, carboxyl, or sulfo groups, because these functional groups are able after activation to react with the reactive groups in hirudin.

The mode of activation of the lipophilic compounds, where appropriate the linkage via a spacer, depends on the functional group and can be carried out in a manner known to the skilled worker.

If the lipophilic compound or the spacer with the lipophilic compound has a carboxyl group, the activation can be take place, for example, by conversion into an alkenyl ester, aryl ester, an O-hemiacetal, O-acylhemiaminoacetal, O-acylhemiketal, O-acylhemiaminoketal, O-acyllactim, symmetrical or unsymmetrical carboxylic anhydride, carboxylic carbamic anhydride, O-acylisoureide, O-acyl-N-alkylhydroxylamine, an O-acylhydroxamic acid, O-acyl-N,N-diacylhydroxylamine, O-acyloxime, O-acyl-N-azo-N-acylhydroxylamine, O-acyl-N-azo-N-arylhydroxylamine, carboxylic sulfurous anhydride, carboxylic sulfuric anhydride, carboxylic phosphorous anhydride, carboxylic phosphoric anhydride, an acyloxyphosphonium compound, a carboxylic phosphoramide anhydride, carbonyl fluoride, or carbonyl chloride, as described in Müller, Houben-Weyl, "Methoden der organischen Chemie", Vol. 15/1 and 15/2, Thieme Verlag, Stuttgart (1974) or Bodanszky, Klausner, Ondetti, "Peptide Synthesis", pages 85–128, John Wiley & Sons, New York, 1976 or other standard works of peptide chemistry.

Particularly suitable reactive groups are carbonyl chloride, symmetric anhydrides, aryl esters unsubstituted or substituted by 1, 2, 3 or 5 halogen or nitro groups, or N-hydroxysuccinimide esters, N-hydroxyphthalimide esters or N-hydroxybenzotriazole esters.

Sulfo groups can be activated in a similar way.

If the functional groups in the lipophilic compounds are amino or hydroxyl groups, the linkage of the lipophilic compounds to the hirudin preferably takes place via a spacer which has as second functional group a carboxyl or sulfo group and is activated in the manner described above for the coupling to the hirudin.

Also very suitable as lipophilic compounds are alkyldiketenes which can be linked directly, without activation, to the hirudin.

Alkyldiketenes which are preferably used are compounds of the general formula III

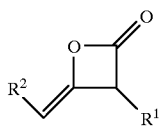

where

R$^1$ and R$^2$ are each, independently of one another, $(CH_2)_m$—$C(R^3)(R^4)$—$(CH_2)_n$—$(CH=CH-CH_2)_o$—$CH_3$, m is 0–28, n is 3–6, o is 0–6 and R$^3$ and R$^4$ are each, independently of one another, H, $C_{1-6}$-alkyl, $C_{3-6}$-cycloalkyl, aryl or benzyl, unsubstituted or substituted by halogen, nitro, cyano, alkyl, alkoxy, alkylthio or haloalkyl groups.

Particularly preferred compounds of the general formula III are fatty alkyldiketenes which are derived, as described, for example, in DE 2927118, from the saturated fatty acids caproic acid, caprylic acid, capric acid, lauric acid, myristic acid, palmitic acid, stearic acid, arachidic acid and behenic acid and the unsaturated fatty acids palmitoleic acid, oleic acid, linoleic acid, linolenic acid, ricinoleic acid, octadecatetraenoic acid, eicosaenoic acid, eicosadienoic acid, arachidonic acid, eicosapentaenoic acid or erucic acid.

It is also possible to use fatty alkyldiketenes derived from mixtures of fatty acids as obtained in the saponification of natural fats such as coconut fat, palmnut oil, rape oil, olive oil, sunflower oil, high oleic sunflower oil, castor oil or beef tallow.

The hirudin conjugates described according to the invention are exactly defined chemically and have a more favorable profile of pharmacological action than hirudin. Inter alia, they have a considerably longer biological activity and better bioavailability. Furthermore, the hydrophobic hirudins permit the active substance to be targeted on the surfaces of blood cells and blood vessels.

Because of these properties, the hirudin conjugates according to the invention are valuable drugs for the treatment and prophylaxis of thrombin-dependent thromboembolic events such as deep vein thrombosis, pulmonary embolism, myocardial or cerebral infarcts and unstable angina, and for the therapy of disseminated intravascular coagulation (DIC) and as comedication with thrombolytics such as streptokinase, urokinase, prourokinase, t-PA, APSAC, plasminogen activators from the salivary glands of animals, and the recombinant and mutated forms of all these substances, to shorten the reperfusion time and prolong the reocclusion time.

Another area of use is to prevent thrombin-dependent early reocclusion and late restenosis after PTCA, to prevent thrombin-induced proliferation of smooth muscle cells, to prevent accumulation of active thrombin in the CNS (e.g. in Alzheimer's disease), to control tumors and to prevent mechanisms which lead to the adhesion and metastasis of tumor cells.

The novel compounds can be used in conventional solid or liquid pharmaceutical forms, e.g. as solutions, ointments, creams or sprays. These are produced in a conventional way. The active substances can for this purpose be processed with conventional pharmaceutical aids such as bulking agents, preservatives, flow regulators, wetting agents, dispersants, emulsifiers, solvents and/or propellant gases (cf. H. Sucker et al: Pharmazeutische Technologie, Thieme-Verlag, Stuttgart, 1978).

The hydrophobic properties also permit the novel hirudin derivatives to be administered transdermally, in particular in conjunction with penetration promoters such as dimethyl sulfoxide, alcohols or azones, or by iontophoresis.

The dosage depends on the age, condition and weight of the patient and on the mode of administration. The daily dose of active substance is, as a rule, about 20–40,000 ATU/kg of body weight, depending on the administration form and indication.

The hirudin conjugates can also be used successfully for the antithrombogenic coating of artificial surfaces such as hemodialysis membranes and the tubing systems required therefor, in vessel replacement or in heart-lung machines.

The following examples describe the invention further.

EXAMPLE 1

Octyldiketene 400.1 g of N,N-dimethylcyclohexylamine were dissolved in 2 l of toluene at 50–60° C. and, at this temperature, 487.5 g of octanoyl chloride were added dropwise in 2.5 h. The mixture was then stirred at 50–60° C. for two hours and cooled to room temperature.

The mixture was washed with ice-cold 1 N sulfuric acid, water and saturated sodium chloride solution, and the organic phase was dried over magnesium sulfate. The crude product was purified by fractional distillation. The main fraction comprised 317.3 g of a colorless liquid which boiled at 135° C. under 0.3 mbar. GC analysis showed that the product comprises 97% octyldiketene. IR, $^1$H and $^{13}$C NMR spectra are consistent with the proposed structure.

EXAMPLE 2

Coupling of octyldiketene to hirudin

The hirudin used was a hirudin mutein which differs from natural hirudin HV1 by the following amino-acid exchanges: Pos. 27:Lys; Pos. 33:Lys; Pos. 36:Arg; Pos. 47:Arg. The preparation of this hirudin mutein is described in DE 40 14 260.

20 mg of hirudin mutein were dissolved in 1 ml of 100 mM sodium borate buffer pH 9.0, and 1 ml of n-propanol and 1.5 mg of octyldiketene were added and the mixture was then incubated with vigorous stirring at 4° C.

After reaction for 30 minutes, the unreacted octyldiketene was removed by extraction with n-hexane (1 vol/vol). The resulting mixture was diluted 50-fold with 0.1% TFA/H$_2$O and loaded onto a Hi-Pore RP 304 column (250×4.6 cm, Biorad, No. 125-0550) and developed with the following gradient:

Solution A: 0.1% TFA/H$_2$O

Solution B: 0.1% TFA/acetonitrile

Flow rate: 1 ml/min

Detection: 216 nm

| Time (min) | % B |
|---|---|
| 0 | 0 |
| 40 | 50 |
| 40.5 | 100 |
| 45 | 100 |
| 45.5 | 0 |

The hirudin-diketene complexes are eluted under the following conditions:

| | % B |
|---|---|
| 1 Diketene unit per hirudin (octyldiketene$_1$-hirudin) | 56% |
| 2 Diketene unit per hirudin (octyldiketene$_2$-hirudin) | 60% |
| 3 Diketene unit per hirudin (octyldiketene$_3$-hirudin) | 68% |

The specific activity of the derivatives isolated from the coupling mixture was

| | ATU/mg |
|---|---|
| Octyldiketene$_1$-hirudin | 7,000 |
| Octyldiketene$_2$-hirudin | 8,000 |
| Octyldiketene$_3$-hirudin | 4,900 |

(determined by a thrombin inhibition assay with the chromogenic substrate S 2238 (Kabi-Pharmacia), FEBS-Lett. 164 (1983), 307, protein determination by UV extinction ($\epsilon_{molar}$=3148, $^1/_{mol.cm}$; $\lambda$=278 nm)

EXAMPLE 3

Hexyldiketene 272.2 g of N,N-dimethylcyclohexylamine were introduced into 1 l of toluene, and water was removed azeotropically for 2 h. The mixture was cooled to 50–60° C., 269 g of hexanoyl chloride were added dropwise, and the mixture was stirred at 55° C. for two hours.

The mixture was washed with 1 N sulfuric acid, water and saturated brine, and the organic phase was dried over magnesium sulfate. The crude product was purified by fractional distillation. The main fraction comprised 172.8 g of a colorless liquid which boiled at 95–100° C. under 0.15 mbar. The product comprises, according to GC analysis, 98% hexyldiketene. IR, $^1$H and $^{13}$C NMR spectra are consistent with the proposed structure.

EXAMPLE 4

Coupling of hexyldiketene to hirudin

Hexyldiketene was coupled to hirudin as in Example 2. 20 mg of hirudin mutein dissolved in 2 ml of 50% n-propanol, 50 mM sodium carbonate pH 9.5 are used for the reaction. The product mixture after stopping (see Example 2) is separated on an RP 304 HPLC column (Biorad No. 125-0550) with the following gradient:

Solvent A: 5 mM ammonium acetate pH 6.5
Solvent B: methanol
Flow rate: 1 ml/min
Detection: 216 nm

| Time (min) | % B |
|---|---|
| 0 | 0 |
| 5 | 30 |
| 30 | 70 |
| 30.1 | 100 |
| 35.0 | 100 |
| 35.1 | 0 |

The hexyldiketene$_1$-hirudin, hexyldiketene$_2$-hirudin and hexyldiketene$_3$-hirudin elute in the gradient at 42.5, 44 and 50% solvent B. The specific activity was determined as described in Example 2 and was 5,700 ATU/mg for the hexyldiketene$_3$-hirudin.

EXAMPLE 5

Sunflower fatty acid chloride 70.5 g of sunflower fatty acid from high oleic sunflower oil with an oleic acid content of 89% and acid number 219 were dissolved in 250 ml of toluene and heated to 40° C. At this temperature, 41.2 g of oxalyl chloride were added dropwie, and the mixture was then stirred for two hours.

The solvent was removed by distillation at 60° C. under reduced pressure. 75 g of sunflower fatty acid chloride were obtained as a yellow oil with chloride number 12.0.

EXAMPLE 6

Alkyldiketene from sunflower fatty acid chloride (sunnyldiketene)

65 g of sunflower fatty acid chloride with chloride number 12.0 were introduced into 400 ml of toluene and heated to 50° C. At this temperature, 33.7 g of N,N-dimethylcyclohexylamine were added dropwise over the course of 25 min. The mixture was kept at 50° C. for two hours and then cooled to room temperature.

The solid was removed by pressure filtration, and the organic phase was washed with 1 M sulfuric acid, saturated sodium bicarbonate solution and saturated sodium chloride solution. The organic phase was dried over magnesium sulfate and the solvent was then removed by distillation under reduced pressure. The residue comprised 51.8 g of a pale yellow oily liquid which, according to $^1$H and $^{13}$C NMR, comprised 95% alkyldiketene.

EXAMPLE 7

Preparation of sunnyldiketene-hirudin 20 mg of hirudin mutein (as in Example 2) were dissolved in 2 ml of 50% n-propanol, 50 mM potassium carbonate buffer pH 9.5, 8.5 mg of sunnyldiketene were added, and the mixture was incubated with vigorous stirring at 20° C. for 60 min. The excess diketene was extracted after the reaction time with n-hexane (1 vol/vol). The product mixture was loaded onto an RP-304 HPLC column (Bio-Rad, No. 125-0550; 250×4.6 cm) and the column was then eluted with the following gradient:

Solvent A: 5 mM ammonium acetate pH 6.5
Solvent B: methanol
Flow rate: 1 ml/min
Detection: 216 nm

| Time (min) | % B |
| --- | --- |
| 0 | 0 |
| 5 | 70 |
| 30 | 95 |
| 30.1 | 100 |
| 35.0 | 100 |
| 35.1 | 0 |

The sunnyldiketene-hirudin conjugates $sunnyl_1$-hirudin, $sunnyl_2$-hirudin and $sunnyl_3$-hirudin elute at 77%, 80% and 90% methanol.

The specific activities were determined as in Example 2 and were:

7,700 ATU/mg for $sunnyl_1$-hirudin 7,100 ATU/mg for $sunnyl_2$-hirudin 6,100 ATU/mg for $sunnyl_3$-hirudin

EXAMPLE 8

Reaction of palmitic acid N-hydroxysuccinimide ester with hirudin 20 mg of hirudin mutein (as in Example 2) were dissolved in 1 ml of 100 mM sodium carbonate pH 9.5, and 1 ml of a solution of 1.5 mg of palmitic acid N-hydroxysuccinimide ester (Sigma) in 1,4-dioxane was added, and the mixture was stirred at 20° C. After 4 h the reaction with the hirudin was stopped by adding a 5-fold molar excess of butylamine (one hour at room temperature).

The product mixture was fractionated on an RP-304 HPLC column (Biorad 125-0550) with the following gradient:

Solvent A: 5 mM ammonium acetate pH 6.5

Solvent B: 100% methanol

Flow rate: 1 ml/min

Detection: 216 nm

| Time (min) | % B |
| --- | --- |
| 0 | 0 |
| 5 | 40 |
| 30 | 90 |
| 30.1 | 100 |
| 35 | 100 |
| 35.1 | 0 |

Palmitic $acid_1$-hirudin elutes at 57%, palmitic $acid_2$-hirudin at 62% and palmitic $acid_3$-hirudin at 76% solvent B.

EXAMPLE 9

Preparation of oleic acid-hirudin 2 g of oleic anhydride were dissolved in 4 ml of dioxane, 460 mg of N-hydroxysuccinimide were added, and the mixture was stirred at room temperature for 2 h. 200 µl of this solution of activated oleic acid were then mixed with 20 ml of n-propanol and 20 ml of a hirudin solution (20 mg/ml) in 0.1 M sodium carbonate or sodium borate pH 9 and incubated at room temperature for 4 h. The reaction was stopped by adding ethanolamine (2-fold molar excess based on oleic acid).

2 ml of the coupling mixture were diluted with 40 ml of 20 mM sodium phosphate buffer pH 7.0, 3.5 M NaCl (solvent A) and loaded onto a TSK-butyl column (1 cm×28 cm; vol: 22 ml, loading 2 mg/ml of gel), and the column was washed at a flow rate of 2 ml/min with 6 column volumes (CV) of solvent A and was developed with the following gradients (solvent B: 20 mM sodium phosphate pH 7.0):

1. 2.5 CV of 70% B
2. 2.5 CV of 80% B
3. 2.5 CV of 90% B
4. 2.5 CV of 100% B
5. 2.5 CV of 30% methanol in B
6. 2.5 CV of 40% methanol in B The hirudin derivatives eluted at 100% B (oleic $acid_1$-hirudin and oleic $acid_2$-hirudin) and 30% methanol (oleic $acid_3$-hirudin). The specific activities were 11,000 U/mg for oleic $acid_1$-hirudin, 6,200 U/mg for oleic $acid_2$-hirudin and 6,600 U/mg for oleic $acid_3$-hirudin.

EXAMPLE 10

Preparation of cholesterol-hirudin 1 ml of a hirudin slution (20 mg/ml in 0.1 M sodium carbonate or sodium borate pH 9.5) were mixed with a solution of cholesterol activated with 3.2 mg of N-hydroxysuccinimide in 1.2 ml of THF and incubated at room temperature for 4 h. The reaction was stopped by adding ethanolamine (2-fold molar excess based on cholesterol), and the pH was adjusted to 7.0.

2 ml of the coupling mixture were diluted with 8 ml of ammonium acetate solution (2 mM, pH 6.0, solvent A) and loaded at a flow rate of 2.5 ml/min onto a HiPore BioRad RP 304 column (10×250 mm) and developed with the following gradient:

| minutes | % B |
| --- | --- |
| 0 | 0 |
| 10 | 40 |
| 60 | 90 |

The cholesterol-hirudin eluted at 38 minutes. The specific activity of the derivative was 16,000 U/mg.

The activated cholesterol was prepared as follows:

15.0 g of 2β-cholesterol and 5.2 g of succinic anhydride in 40 ml of pyridine were refluxed for 22 h and then taken up in 250 ml of MTBE. The organic phase was extracted with 200 ml of 1N hydrochloric acid, 200 ml of water and 200 ml of saturated sodium chloride solution and stirred with magnesium sulfate and active carbon. Solvent was removed from the filtrate under reduced pressure to result in 18.1 g of cholest-5-en-3β-yl succinate.

1.94 g of this ester and 0.55 g of N-hydroxysuccinimide were introduced into 12 ml od dichloromethane at 4° C., and 1.01 g of N,N-dicyclohexylcarbodiimide were added. The mixture was allowed to warm to room temperature and was stirred overnight, and the solid was filtered off. The crude product present in the organic phase was chromatographed on 80 g of silica gel (dichloromethane+ethyl acetate=2+1) to obtain 1.7 g of cholesterol activated with N-hydroxysuccinimide (N-[3-cholest-5-en-3β-yloxycarbonyl)propionyloxy]-succinimide).

EXAMPLE 11

Preparation of farnesylhirudin 5.6 ml of a hirudin solution (21 mg/ml in 0.1 M sodium carbonate pH 9) were diluted with 5.5 ml of n-propanol, 32 mg of farnesyl alcohol p-nitrophenyl carbonate were added, and the mixture was incubated while stirring at room temperature for 12 h. The mixture was then diluted with 150 ml of 2 M NaCl, 20 mM sodium phosphate pH 7 and loaded onto a t-butyl column (Loading 2 mg of protein/ml of gel, column height 25 cm). The column was then washed with 2.2 column volumes of loading buffer and then developed with a linear gradient from 2 M NaCl, 20 mM sodium phosphate pH 7 to 20 mM sodium phosphate pH 7 (25 column volumes). The farnesylhirudin eluted at the end of the gradient at 20 mM sodium phosphate. The specific activity was determined as in Example 2 and was 11,300 U/mg.

The farnesyl alcohol p-nitrophenyl carbonate was prepared as follows:

1.40 g of farnesol and 1.01 g of diazo[2.2.2]bicyclooctane [sic] were dissolved in 20 ml of dichloromethane, and 3.63 g of p-nitrophenyl chloroformate in 10 ml of dichloromethane were added dropwise over the course of 15 minutes. The mixture was stirred for 1.5 h, the solvent was removed under reduced pressure, and the crude product was chromatographed on 150 g of silica gel (hexane+ethyl acetate=20+1) to obtain 2.2 g of farnesyl alcohol p-nitrophenyl carbonate.

EXAMPLE 12

Preparation of stearic acid-hirudin 0.5 g of stearoyl chloride was dissolved in 2 ml of 1,4-dioxane, and 0.29 g of N-hydroxysuccinimide and 0.1 ml of triethylamine were added, and the mixture was stirred at room temperature for 3 h. 1 ml of water was added to the mixture, and the pH was adjusted to 5 by addition of alkali. 60 µl of a succinimide-activated stearic acid solution were mixed with 2.5 ml of hirudin solution (21 mg/ml in 0.1 M sodium carbonate pH 9) and 2.5 ml of dioxane, and the mixture was incubated at room temperature with stirring for 12 h. The mixture was then purified by preparative RP-HPLC (see Example 2). The derivatives elute at 48% B, 54% B, 62% B and 74% B. The specific acitivities were 9,600 U/mg, 12,400 U/mg, 12,800 U/mg and 840 U/mg.

EXAMPLE 13

Preparation of Lutensol T03-hirudin 0.5 ml of a hirudin solution (21 mg/ml in 0.1 M sodium carbonate or sodium borate pH 9) was diluted with 0.5 ml of tetrahydrofuran, 1.2 mg of Lutensol T03 N-hydroxysuccinimide carbonate (Example 12) were added, and the mixture was incubated with stirring at room temperature for 12 h. The reaction was stopped by adding ethanolamine (2-fold molar excess based on activated Lutensol) and fractionated by chromatography as described in Example 10. The hirudin-Lutensol derivatives eluted at 45% B (derivative 1 [lacuna] 11,300 U/mg, for derivative 2 9,700 U/mg and 440 U/mg for derivative 3.

The starting material was prepared as follows:

20 g of phosgene were condensed in 100 ml of toluene at 0° C., and 34.0 g of Lutensol T03 (OH number=165) in 50 ml of toluene were added dropwise over the course of 10 min. The mixture was allowed to warm to room temperature, and the solvent was removed under oil pump vacuum at 35° C. 40.3 g of the chlorocarbonate of Lutensol T03 were obtained.

1.2 g of N-hydroxysuccinimide and 1.0 g of triethylamine were dissolved in 20 ml of dichloromethane, and 3.92 g of the chlorocarbonate of Lutensol T03 in 10 ml of dichloromethane were added dropwise over the course of 5 min. The mixture was left to stir at room temperature for 2 h, the solvent was removed under reduced pressure, and the residue was taken up in ethyl acetate. The remaining solid was separated off, and the solvent was removed from the filtrate under reduced pressure to afford 4.3 g of the N-hydroxysuccinimide carbonate of Lutensol T03.

EXAMPLE 14

Preparation of octyldiketene-phenylalanine-hirudin 0.5 ml of a hirudin solution (21 mg/ml in 0.1 M sodium carbonate or sodium borate pH 9) was diluted with 0.5 ml of tetrahydrofuran, and 4 mg of N-(2-hexyl-3-oxodecanoyl) phenylalanine N-hydroxysuccinimide ester were added, and the mixture was incubated with stirring at room temperature for 12 h. The reaction was stopped by adding ethanolamine (2-fold molar excess based on activated phenylalanine) and fractionated by RP-HPLC as described in Example 10. The hirudin-diketene derivatives eluted at 43% B (derivative 1), 48% B (derivative 2) and 58% B (derivative 3). The specific activities were determined as in Example 2 and were 930 U/mg for derivative 1, 2,800 U/mg for derivative 2 and 135 U/mg for derivative 3.

The starting material was prepared as follows:

82.5 g of phenylalanine were introduced into 500 ml of water at pH 13.5, and 145.9 g of octyldiketene in 50 ml of dichloromethane were added dropwise over the course of 1.25 h. The suspension was vigorously stirred for 5 h, 2.5 l of water were added, and the pH was adjusted to 1 with concentrated hydrochloric acid. The aqueous phase was extracted with a total of 2.5 l of dichloromethane, the collected organic phases were dried over magnesium sulfate, and the solvent was removed under reduced pressure. The resulting white solid was stirred in 1,000 ml of pentane, and the solid was filtered off and dried at 60° C. under reduced pressure to result in 190 g of N-(2-hexyl-3-oxodecanoyl) phenylalanine.

N-(2-Hexyl-3-oxodecanoyl)phenylalanine and 0.55 g of N-hydroxysuccinimide were introduced into 10 ml of dichloromethane and, at 4° C., 1.01 g of N,N-dicyclohexylcarbodiimide were added. The mixture was allowed to warm to room temperature, the solid was separated off, and the crude product contained in the phase [sic] was chromatographed on 80 g of silica gel (dichlorohexane [sic]+hexane=3+1; 1% glacial acetic acid). 2.0 g of N-(2-hexyl-3-oxodecanoyl)phenylalanine N-hydroxysuccinimide ester were obtained.

EXAMPLE 15

Preparation of octyldiketene-caproic acid-hirudin 1.0 ml of a hirudin solution (21 mg/ml in 0.1 M sodium carbonate or sodium borate pH 9) was diluted with 1.0 ml of tetrahydrofuran, and 7 mg of N-(6-(2-hexyl-3-oxodecanoylamino)hexanoyloxy)succinimide were added, and the mixture was incubated with stirring at room temperature for 12 h. The reaction was stopped by adding ethanolamine (2-fold molar excess based on activated diketene) and fractionated by RP chromatography as described in Example 10. The hirudin-diketene derivatives eluted at 48% B (derivative 1), 52% B (derivative 2) and 63% B (derivative 3). The specific activities were determined as in Example 2 and were 7,500 U/mg for derivative 1, 3,400 U/mg for derivative 2 and 80 U/mg for derivative 3.

The starting material was prepared as follows:

6.55 g of 6-aminocaproic acid were dissolved at pH 9 in 100 ml of water, and 14.24 g of octyldiketene were added dropwise over the course of 20 min. The mixture was stirred overnight, the pH was adjusted to 1 with concentrated hydrochloric acid, and the aqueous phase was extracted with 100 ml of MTBE. The organic phase was dried over magnesium sulfate, the solvent was removed under reduced pressure, and the crude product was stirred in 150 ml of pentane. The resulting solid was filtered off and dried at 60° C. under reduced pressure to afford 5.9 g of 6-(2-hexyl-3-oxodecanoylamino)hexanoic acid.

1.53 g of the resulting product and 0.55 g of N-hydroxysuccinimide were introduced into 10 ml of dichloromethane at 4° C. and 1.01 g of N,N-dicyclohexylcarbodiimide were added. The mixture was allowed to warm to room temperature and stirred overnight, and the solid was filtered off. The crude product containing [sic] in the organic phase was chromatographed on 80 g of silica gel (ethyl acetate+hexane=3+5; 1% glacial acetic acid) to afford 1.7 g of N-[6-(2-hexyl-3-oxodecanoylamino) hexanoyloxy]succinimide.

EXAMPLE 16

Kinetics of the anti-factor IIa activity in plasma samples from dogs and rats

Method: hirudin conjugates or placebo were administered intravenously to anesthetized rats or conscious dogs. At defined times, samples of venous blood were taken from the animals to obtain citrated plasma. The free anti-factor IIa activity of the hirudin conjugates in the plasma was determined by a chromogenic assay using a standard plot with recombinant hirudin.

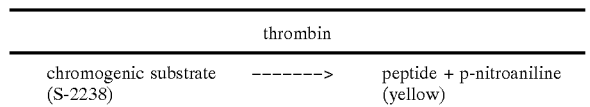

|  | thrombin |  |
|---|---|---|
| chromogenic substrate (S-2238) | -------> | peptide + p-nitroaniline (yellow) |

In microplates, 10 μl of plasma sample and 100 μl of thrombin (0.3 NIH units/ml) are pipetted in each case into 100 μl of tris buffer (tris 200 mmol/l, NaCl 25 mmol/l, pH 8.1). After 1 min, the reaction is started by adding 50 μl of substrate solution (S-2238, 1.34 mmol/l). The mixture is briefly mixed and then incubated at 25° C. for 5 min, after which the reaction is stopped by adding 100 μl of 30% strength acetic acid. The extinction of the sample measured at 405 nm relative to 630 nm is inversely proportional to the anti-factor IIa activity in the plasma sample. In some cases the thrombin time (TT) and partial thromboplastin time (APTT) were also measured in the plasma samples.

Figure 2:
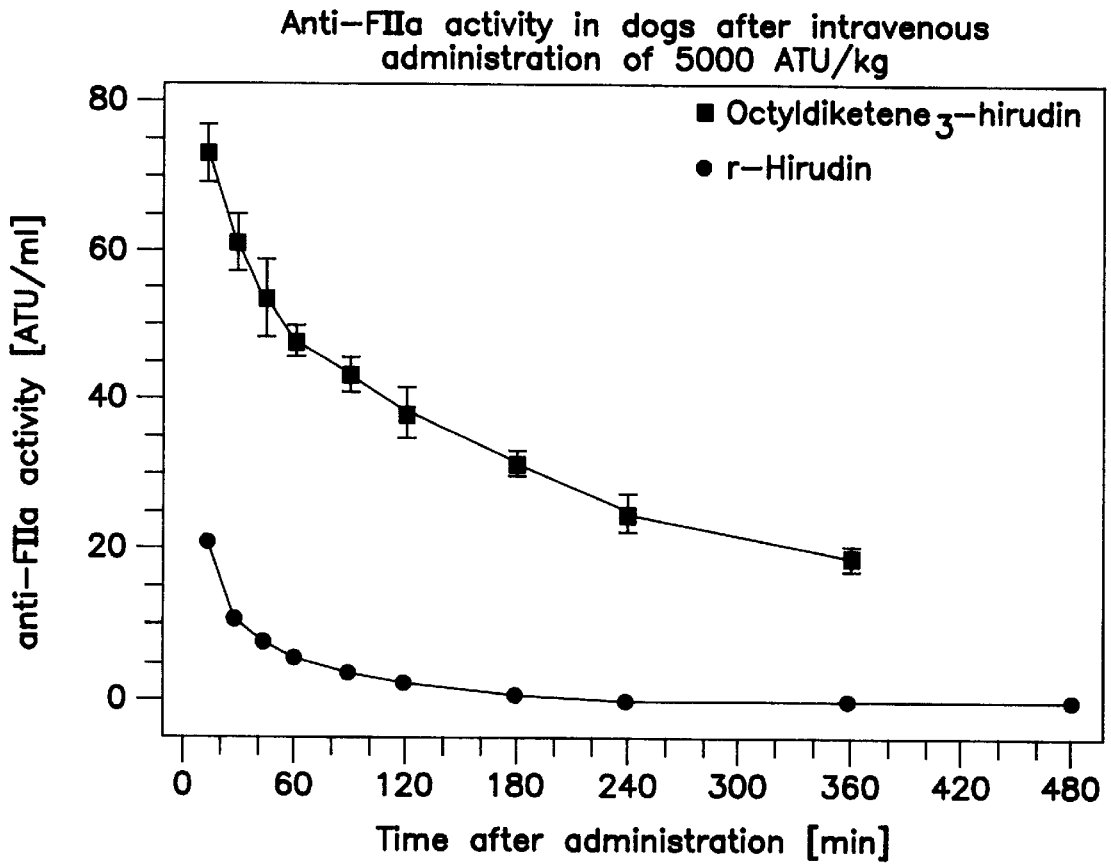
FIG. 2: Anti-FIIa activity in dogs after intravenous administration of 5000 ATU/kg of Octyldiketene$_3$-hirudin and r-Hirudin.
Figure 3:
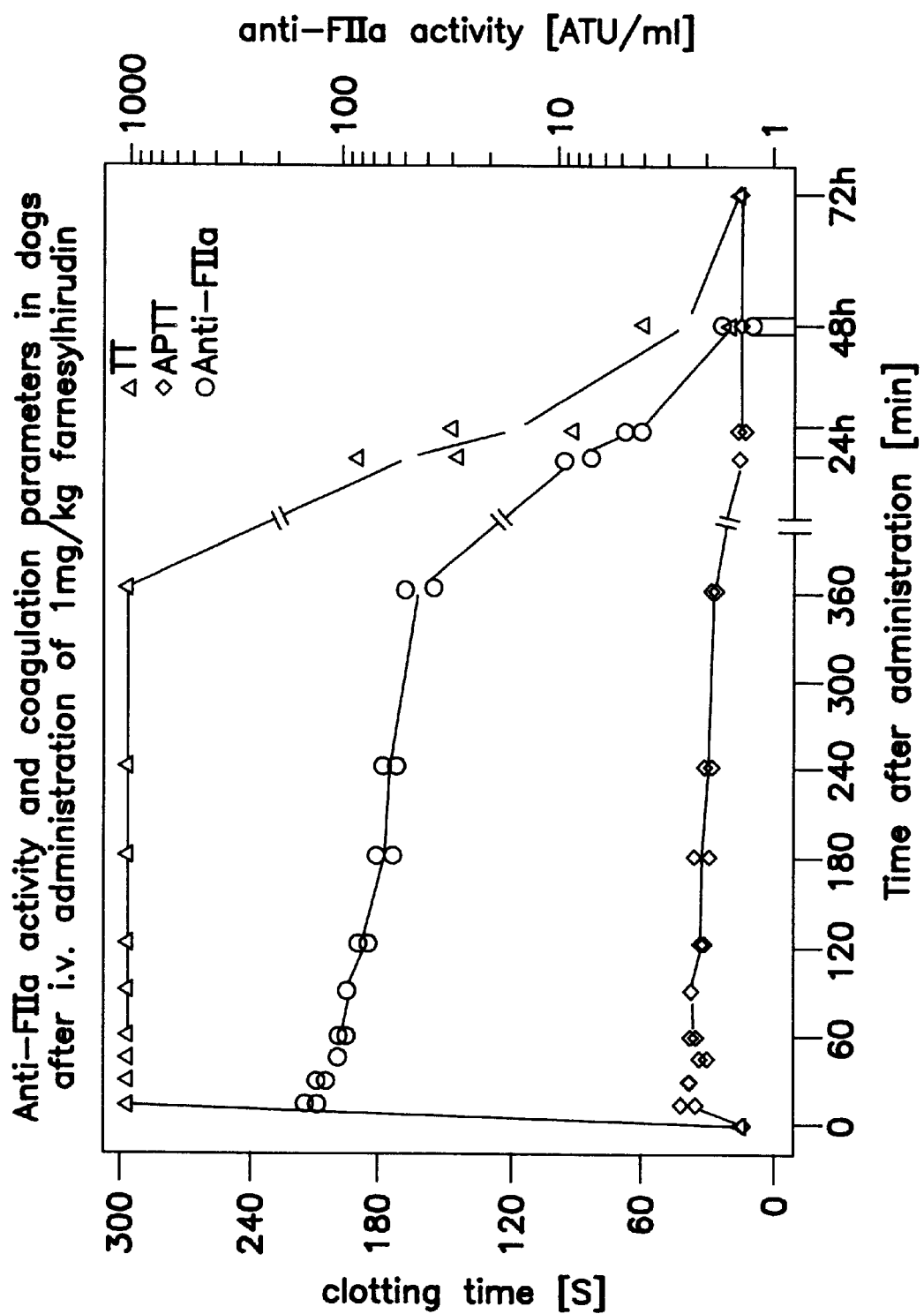
FIG. 3: Anti-FIIa activity after i.v. administration of 1 mg/kg farnesylhirudin.

Results:

With approximately the same specific activity, the decline in the free anti-factor IIa activity was found to be distinctly slower after i.v. administration of 1 mg/kg lipophilic hirudin derivatives to anesthetized rats by comparison with r-hirudin (FIG. 1). In dogs, after i.v. administration of 5,000 anti-thrombin units/kg (ATU/kg) of octyldiketene$_3$-hirudin there was likewise found to be a distinctly higher active level with slower elimination compared with r-hirudin (FIG. 2). A very slow decrease in the free anti-factor IIa activity was also observed after i.v. administration of 1 mg/kg farnesylhirudin (FIG. 3).

EXAMPLE 17

Thrombin-induced aggregation of washed platelets from the blood of humans and rats ex vivo and in vitro after previous incubation of platelets with lipophilic hirudin derivatives Method: fresh citrated blood (9 parts of blood+1 part of sodium citrate 0.11 mol/l, rat: 8.5+1.5) is centrifuged at 250 xg for 16 min to obtain platelet-rich plasma (PRP, supernatant). A concentrate of washed platelets is obtained from the PRP by a method of Patscheke et al. (Haemostasis 10, 1981, 14–27). This entails the platelets initially being sedimented from the PRP by centrifugation at 330×g for 7 min. If treatment with hirudin derivatives is to take place, at this point addition of 200 μl of the derivative in a washing solution (120 mmol/l NaCl, 5 mmol/l KCl, 2 mmol/l CaCl$_2$, 1 mmol/l MgCl$_2$, 5 mmol/l glucose, 2 g/l albumin, 50 mg/l apyrase in 30 mmol/l sodium phosphate, pH 6.5) for a final concentration of 0.215 mg/l for the derivative is followed by vortexing the pellet and incubating at room temperature for 10 min. This is followed by two washing steps in this washing solution, and then the platelets are finally resuspended in an assay medium containing 120 mmol/l NaCl, 5 mmol/l KCl, 1 mmol/l CaCl$_2$, 0.1 mmol/l MgCl$_2$, 5 mmol/l glucose, 0.5 g/l albumin, 50 mg/l apyrase, 1 mmol/l sodium phosphate, TES/NaOH, pH 7.4. The platelet count was adjusted to $2 \times 10^5/\mu l$ (rat $8 \times 10^6/\mu g$). To determine platelet aggregation, 218 μl of the platelet concentration are incubated in an aggregometer (PAP-4 Bio Data Corporation) at 37° C. for 3 min, stirred at 1,000 rpm for 1 min and incubated once more for 1 min. The aggregation is then started by adding 2 μl of thrombin solution. The platelet aggregation is determined from the change in the measured transmission of the sample per unit time (slope method). As a measure of the relative activity and affinity of the hirudin derivatives, the EC50 is determined as the thrombin concentration in NIH units/ml at which half the maximum gradient of platelet aggregation is reached. The neutralization index (NI) is calculated from this EC50 and the EC50 of a sample preincubated without hirudin from NI=EC50 derivative/EC50 control. This value is derivative-specific and indicates the factor by which the thrombin concentration as agonist must be raised in order again to reach the same aggregation (half-maximum gradient) as in the control.

Figure 4:
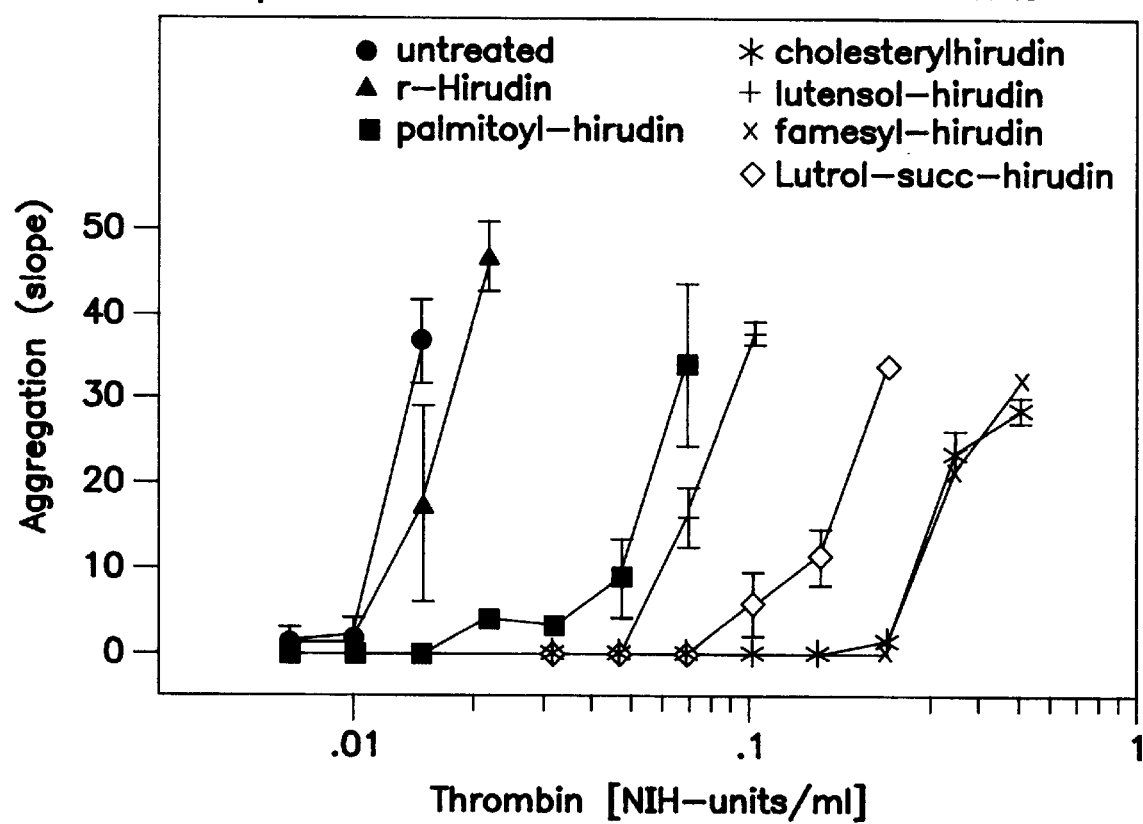
FIG. 4: Thrombin-induced aggregation of washed platelets after pretreatment with r-Hirudin, palmitoyl-hirudin, cholesterylhirudin, lutensol-hirudin, famesyl-hirudin, and Lutrol-succ-hirudin.

Results:

After preincubation of platelets from different species with 21.5 μg/ml lipophilic hirudin derivatives it was necessary in some cases to use a multiple of the thrombin concentration employed for the control in order to achieve aggregation again (FIG. 4). This inhibition is brought about by the immunologically detectable adhesion of the lipophilic hirudin derivatives to the platelets. The neutralization indices reach values of up to 25 with human platelets (Table 1). 24 h after administration of 10 mg/kg cholesterylhirudin to rats the NI was found on washed platelets ex vivo to be still 5.4 (see Example 20, Table 2).

TABLE 1

Neutralization indices (NI) for selected compounds on human platelets

| Substance | NI |
|---|---|
| Control (placebo-treated) | 1 |
| r-Hirudin | 1.21 |
| Stearoylhirudin | 5.42 |
| palmitoylhirudin | 4.71 |
| Cholesterylhirudin | 21.2 |
| Lutensol T03-hirudin | 15.1 |
| Farnesylhirudin | 24.3 |

EXAMPLE 18

Antithrombotic effect in an arteriovenous shunt, rats

Method: In this experiment, a glass capillary in an arteriovenous shunt acts as artificial thrombogenic surface and induces thrombosis. The anesthetized (urethane 25%, 2×8 mg/kg i.p.) rat is fixed on its back on a stage maintained at 37° C. The right carotid artery and jugular vein are exposed and short polyethylene catheters (Portex, PE 50) are implanted, filled with NaCl solution and occluded by clips. The free ends of the catheters are linked by a 20.0 mm long glass capillary (internal diameter 1.0 mm) which acts as thrombogenic surface. The test substance can be administered i.v., s.c., orally or as infusion. After the required incubation time (5, 60 or 360 min) with the test substance or solvent (control), the shunt is opened by removing the clips. The blood flow through the shunt leads to a rapid rise in its temperature, which is measured in the middle of the glass capillary. The increase from room temperature to body temperature is an indicator of the patency of the shunt. The temperature is recorded continuously until the shunt occludes, but for no more than 30 minutes. To compare the activities of different hirudin derivatives, the ED15 min is calculated as the dose which increases the occlusion time by 15 min compared with the control group. In addition, when the shunt is opened and at the end of the experiment, blood samples are taken to determine the anti-FIIa activity in the plasma.

Figure 5:
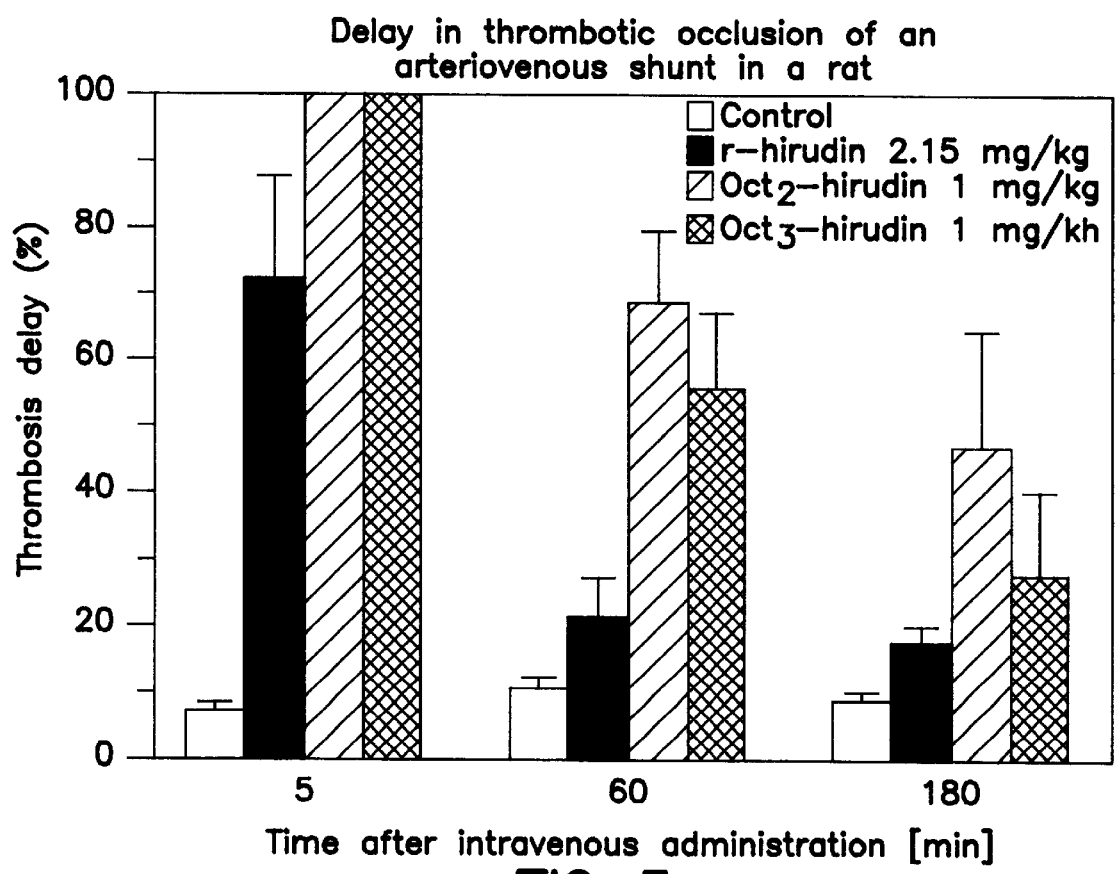
FIG. 5: Delay in thrombotic occlusion of an arteriovenous shunt in a rat after intravenous administration of r-Hirudin, Oct$_2$- hirudin, and Oct$_2$-hirudin.

Results: Octyldiketene-hirudin$_3$ [sic] and octyldiketene$_3$-hirudin show, because of their longer duration of action, antithrombotic efficacy at lower doses and over a longer time than does r-hirudin (FIG. 5).

EXAMPLE 19

Antithrombotic effect on current-induced thrombosis in rats

Method: In this experiment, endothelial damage is produced by a brief flow of current through two electrodes attached to the carotid artery, and thus thrombotic occlusion of the vessel is induced. The anesthetized (urethane 25%, 2×8 mg/kg i.p.) rat is fixed on its back on a stage maintained at 37° C. A 20 mm long segment of the right carotid artery is exposed and an ultrasonic transit time flow measuring head is placed on the proximal half of the segment. The volume-based flow is continuously recorded during the 30 min observation period by an ultrasonic flow measuring device (T206, Transonic Systems Inc., USA). Thrombus formation is induced by a constant flow of current (3 mA, 1 min) through a pair of hook-shaped electrodes attached to the surface of the vessel 1 cm distal of the flow measuring head. Vascular occlusion is defined as a reduction in the volume-based flow to<0.3 ml/min for more than 3 minutes. The antithrombotic activity of hirudin derivatives is quantified as the frequency of thrombosis in 30 minutes in a group of 10 animals. To compare the activities of different hirudin derivatives, the ED50 is calculated as the dose which reduces the frequency of thrombosis by 50% compared with the control group. Before applying the voltage and at the end of the experiment, additional blood samples are taken to determine the anti-FIIa activity in the plasma.

Results:

The ED50 determined for palmitoyl$_2$-hirudin 5 min after intravenous administration was 0.24 mg/kg. The corresponding ED50 of r-hirudin is 0.47 mg/kg. Even 24 h after intravenous administration of cholesterylhirudin to rats there was still, because of the long duration of action, inhibition of the aggregation of washed platelets ex vivo and good antithrombotic activity (Table 2).

TABLE 2

Antithrombotic effect and inhibition of platelet aggregation by cholesterylhirudin 24 h after i.v. administration (n = 9–10)

| Treatment | Frequency of thrombosis (%) | Neutralization index (NI) in washed platelets | Plasma anti-FIIa activity [ATU/ml] | TT [s] | APTT [s] |
|---|---|---|---|---|---|
| In vitro | — | 18.3 ± 6.1 | — | — | — |
| Placebo | 100 | 1 | 0 | 41 ± 1 | 29 ± 4 |
| 1.0 mg/kg | 50 | 1.5 ± 0.02 | 5.7 ± 0.6 | 267 ± 15 | 30 ± 3 |
| 10 mg/kg | 11 | 5.39 ± 0.74 | 61.0 ± 3.8 | >300 | 52 ± 4 |

We claim:

1. A hirudin conjugate formed from a hirudin molecule covalently linked to one or more lipophilic compounds, where the lipophilic compound has an octanol/water partition coefficient of more than 1.8 and is covalently linked to the hirudin.

2. A hirudin conjugate as claimed in claim 1, wherein the linkage of the lipophilic compound takes place in the region of amino acids 27–37.

3. A hirudin conjugate as claimed in claim 1, wherein the linkage between hirudin and lipophilic compounds takes place via the amino side chains of lysine residues in the hirudin.

4. A hirudin conjugate as claimed in claim 1, wherein 1–3 lipophilic compounds are linked to the hirudin.

5. A hirudin conjugate as claimed in claim 1, wherein at least one lipophilic compound is linked to amino acid 27 or 33.

6. A hirudin conjugate as claimed in claim 1 for use for controlling diseases.

7. A process for preparing hirudin conjugates, which comprises reacting a hirudin with one or more mole equivalents of a lipophilic compound after chemical activation of the lipophilic compound, where appropriate.

* * * * *